United States Patent [19]
Leibinsohn

[11] Patent Number: 4,507,116
[45] Date of Patent: Mar. 26, 1985

[54] APPARATUS FOR THE INDUCED INFUSION OF A LIQUID FROM A FLEXIBLE LIQUID BAG

[76] Inventor: Saul Leibinsohn, 11 Olei Hagardom St., Rishon Lezion, Israel

[21] Appl. No.: 429,674

[22] Filed: Sep. 30, 1982

[30] Foreign Application Priority Data

Apr. 22, 1982 [IL] Israel .................................. 65580

[51] Int. Cl.³ .............................................. A61M 5/00
[52] U.S. Cl. ............................ 604/142; 128/DIG. 12; 222/95; 604/99
[58] Field of Search ................. 604/141, 142, 153, 99, 604/96; 128/DIG. 12, DIG. 15; 138/30; 222/95, 105

[56] References Cited

U.S. PATENT DOCUMENTS

| 3,601,128 | 8/1971 | Hakim | 138/30 |
| 3,895,741 | 7/1975 | Nugent | 222/105 X |
| 4,064,882 | 12/1977 | Johnson | 604/99 X |
| 4,090,514 | 5/1978 | Hinck et al. | 604/142 |
| 4,178,939 | 12/1979 | Stephens | 604/99 X |

Primary Examiner—Stephen C. Pellegrino
Attorney, Agent, or Firm—Benjamin J. Barish

[57] ABSTRACT

Apparatus for the induced infusion of a liquid from a flexible liquid bag comprises a pumping bulb, elastic inflatable means coupled to the bulb for inflation thereby, and a flexible sleeve for retaining the liquid bag firmly against a first portion of the inflatable means for applying the pressure thereof to the bag to induce infusion of the liquid therefrom. The elastic inflatable means includes a second portion which serves as an accumulator for accumulating pressurized fluid pumped by the bulb and comprises an outer non-elastic sheath for limiting the accumulation of the pressurized fluid therein. In one described embodiment, the two mentioned portions of the elastic inflatable means are constituted of separate units, one being a bag-presser including an inflatable bladder against which the liquid bag is pressed by the flexible sleeve, and the other being a separate accumulator including an inflatable tube enclosed by the non-elastic sheath. In a second described embodiment, both of the mentioned portions of the elastic inflatable means are constituted of a single elastic bladder enclosed only at its mid-portion by the flexible sleeve, the end portions of the bladder projecting outwardly of the flexible sleeve and being enclosed by the non-elastic sheath so as to serve as the accumulators for accumulating the pressurized fluid.

16 Claims, 8 Drawing Figures

APPARATUS FOR THE INDUCED INFUSION OF A LIQUID FROM A FLEXIBLE LIQUID BAG

BACKGROUND OF THE INVENTION

The present invention relates to apparatus for the induced infusion of a liquid from a flexible liquid bag, such as involved during a therapeutic treatment or a surgical operation of the patient.

In most cases, liquids are administered to patients by gravity-infusion, but there are a number of situations wherein induced infusion is required. At the present time, this is usually done by including a bag-presser which includes a bladder inflatable by a pumping bulb, and a flexible non-elastic sleeve for retaining the liquid bag firmly pressed against the inflated bladder such that the pressure of the bladder is transferred to the liquid bag to induce the infusion therefrom. An example of such a bag-presser is illustrated in U.S. Pat. No. 3,153,414.

One of the main drawbacks in the use of the known bag-pressers of this type is that the pressure applied by the inflated bladder to the liquid bag changes quite substantially during the decrease in volume of the bag unless the bladder is periodically reinflated to compensate for the loss in volume of the bag. For example, in a typical bag-presser commonly used today, wherein the bladder is inflated to a pressure of 300 mm Hg, a liquid bag of a volume of 500 cc is usually pressurized slightly greater than 300 mm Hg at the start when its initial volume is equal to 500 cc, but its pressure drops to about 300 mm Hg when its volume reaches 400 cc, to about 270 mm Hg when its volume reaches 300 cc, to about 230 mm Hg when its volume reaches 200 cc, to about 200 mm Hg when its volume reaches 100 cc, and to about 180 mm Hg when its volume reaches 50 cc. This drop in pressure during the decrease in volume of the liquid bag may result in the required amount of the liquid not being administered at the required rate or within the required period of time. To avoid this, the infusion procedure must be continuously monitored and the bag-presser bladder reinflated as necessary to maintain the desired rate of infusion, but such continuous monitoring is very demanding of the nurse's time and therefore cannot always be provided.

An object of the present invention is to provide apparatus for the induced infusion of a liquid from a liquid bag which provides a substantially uniform pressure to the liquid bag, and therefore a substantially uniform rate of infusion, until substantially the complete contents of the bag are dispensed.

Another object of the invention is to provide apparatus of the above type having a number of further advantages as will be described more particularly below.

BRIEF SUMMARY OF THE INVENTION

According to a broad aspect of the present invention, there is provided apparatus for the induced infusion of a liquid from a flexible liquid bag, comprising: a hand-operable pumping bulb; elastic inflatable means coupled to the bulb for inflation by a fluid pumped therein by operating the bulb; and a sleeve for retaining the bag firmly pressed against a first portion of the elastic inflatable means for applying the pressure thereof to the bag in order to induce infusion of the liquid therefrom; characterized in that a second portion of the inflatable means serves as an accumulator for accumulating pressurized fluid pumped by the bulb, and comprises an outer non-elastic sheath enclosing the latter portion of the elastic inflatable means for limiting the accumulation of the pressurized fluid therein.

More particularly, in the preferred embodiment of the invention described below, the non-elastic sheath is of flexible material having a substantially larger internal volume than the elastic inflatable accumulator, such that the sheath is normally deflated but also assumes an inflated state when the accumulator has been inflated to the predetermined volume and pressure. Thus, this sheath not only indicates "by feel" when the predetermined pressure is about to be exceeded, but also indicates this by sight, thereby providing better assurance against applying an excessive pressure which could be damaging to the patient.

In one embodiment of the invention described below, the two portions of the inflatable elastic means are separate inflatable units, namely, a bag-presser unit and an accumulator unit including a separate inflatable bladder enclosed by the non-elastic sheath. Thus, in this embodiment, the bag-presser for applying the pressure to the liquid bag could be of substantially smaller volume than commonly used today, since the provision of the accumulator obviates the need for a substantial dead-volume of air in the bag-presser. This is another advantage of the present invention, in that it not only can reduce or eliminate the need for continuous monitoring and re-pumping during the administration of the infusion liquid, but can also reduce the amount of pumping required at the start.

According to another important feature in the preferred embodiment of the invention described below, the accumulator is in the form of an inflatable tube, e.g., of natural or synthetic rubber, loosely enclosed by the flexible non-elastic sheath. The thickness of the tube is determined such that the tube does not actually inflate until the desired pressure for infusion is reached, at which time the tube inflates to accumulate air pressurized at this desired pressure until the inflation of the tube is limited by the non-elastic flexible sheath, thereby indicating, both by feel and visually, that the manual inflation should be terminated.

According to a further important feature in the preferred embodiment of the invention described below, the bag-presser includes a rigid backing plate which is preferably bent so as to form a generally concave face for receiving the inflatable bladder and the liquid bag. Such an arrangement provides a very compact construction, and particularly one in which the pressure applied to the bag more closely conforms to the pressure within the bladder for substantially the complete administering of the liquid from the bag.

Another embodiment of the invention is described below, wherein both the bag-presser and the accumulator functions are performed by a single elastic inflatable bladder. In this described embodiment, the flexible sleeve presses the liquid bag against one portion of the bladder, permitting another portion of the bladder to inflate and thereby to serve as the accumulator, the latter portion of the bladder being enclosed by the flexible non-elastic sheath. More particularly, in the described embodiment, the flexible sleeve retains the liquid bag pressed against the mid-portion of the inflatable bladder, the end portions of the bladder projecting past the flexible sleeve and therefore being permitted to inflate to a greater extent than the mid-portion of the bladder, so that these end portions can serve as the accumulators. In such a construction, both of the end portions of the bladder serve as pressure accumulators and are therefore enclosed by flexible non-elastic sheaths.

According to a still further embodiment of the invention, there is provided an inflatable bag-presser unit for use with an infusion bag, comprising an inflatable bladder, a rigid backing plate on one side of the bladder, and a flexible sleeve adapted to receive the infusion bag and to retain same pressed against the opposite side of the inflatable bladder. In this embodiment, the sleeve is in the form of a flexible strip secured at one end with respect to one end of the rigid backing plate, the flexible strip being wrappable about the rigid backing plate and secured at its opposite end with respect thereto, to enclose the inflatable bladder and infusion bag therebetween.

In the preferred embodiment of the invention, the rigid backing plate is enclosed within a flexible sleeve. The flexible strip is secured at one end to the rigid backing plate sleeve, and at the opposite end it is releasably attached to the rigid backing plate sleeve by releasable fastening means.

Further features and advantages of the invention will be apparent from the description below

BRIEF DESCRIPTION OF THE DRAWINGS

The invention is herein described, by way of example only, with reference to the accompanying drawings, wherein.

DESCRIPTION OF PREFERRED EMBODIMENTS

Embodiment of FIGS. 1-4

Figure 1:
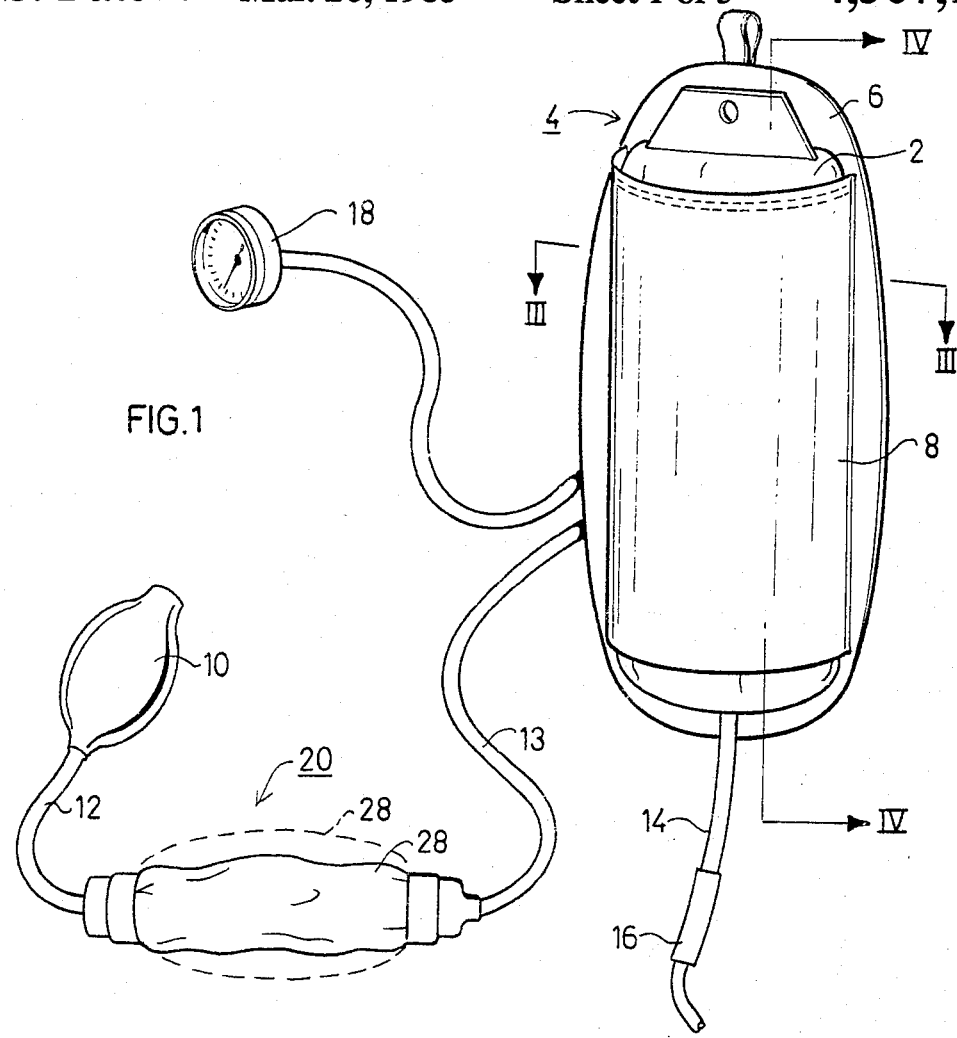
FIG. 1 illustrates one form of apparatus constructed in accordance with the present invention for the induced infusion of a liquid from a flexible liquid bag.

In the embodiment illustrated in FIGS. 1-4, the liquid to be infused is contained within a conventional flexible liquid bag 2 usually of transparent plastic material so as to enable viewing the contents of the bag. Infusion of the liquid contents is induced by a bag-presser 4 including an elastic inflatable bladder 6 such as of rubber, and a flexible sleeve 8 which retains the infusion bag 2 tightly pressed against the bladder when the bladder is inflated. Flexible sleeve 8 is preferably also of transparent or transluscent material to enable viewing contents of the bag. Bladder 6 of the bag-presser 4 is inflated by a hand-operable pumping bulb 10 connected to the bladder via tubing 12, 13; and the liquid in the infusion bag 2 is outletted via tubing 14 and drip chamber 16 to the patient receiving the infusion, usually by means of an intravenous needle (not shown). A manometer 18 is provided to indicate the pressure of the inflated bladder 6, and therefore of the pressure transmitted thereby to the infusion bag 2.

The infusion apparatus illustrated in FIG. 1, insofar as described above, is well-known and in common use. As indicated earlier, however, the pressure applied by the inflatable bladder 6 to the infusion bag 2 decreases quite significantly during the course of the infusion, such as to require frequent monitoring and re-inflating of the bladder if the pressure is not to drop to such a low level that the flow rate may be insufficient for administering the infusion liquid at a prescribed rate.

Figure 2:
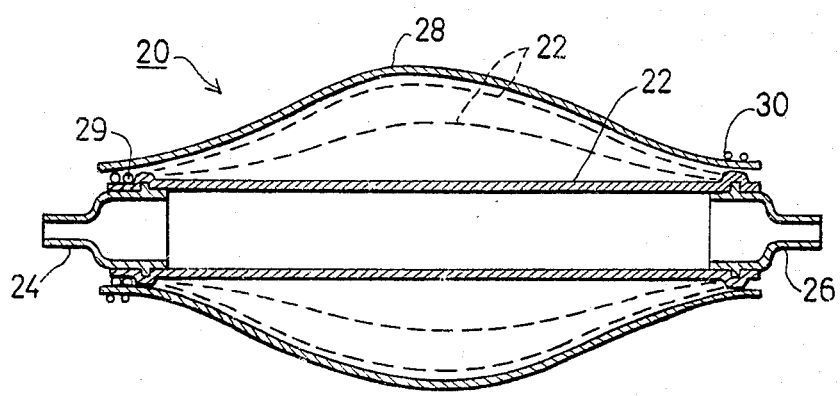
FIG. 2 is an enlarged sectional view illustrating the accumulator device in the apparatus of FIG. 1.

The present invention is primarily concerned with the provision of an accumulator unit, generally designated 20 in FIG. 1 and more particularly illustrated in FIG. 2, which provides a number of important advantages. One important advantage is that it maintains the pressure on the infusion bag substantially constant for the complete administration of the contents of the infusion bag, without the need to monitor or re-pump the inflatable bladder 6 in the bag-presser 4. Other advantages include lessening the danger of over-pressurizing the infusion liquid at the time of its administration, and reducing the size of the unit 4. All these advantages will be described more particularly below.

The structure of the accumulator unit 20 in the apparatus of FIG. 1 is illustrated in FIG. 2. Thus, it includes an elastic tube 22, preferably of natural or synthetic rubber, carrying at one end a connector 24 adapted to be connected to the pumping bulb 10 via tube 12, and at the opposite side a second connector 26 adapted to be connected, via tube 13, to the inflatable bladder 6 of the bag-presser 4. Overlying the elastic tube 22 is an outer sheath 28 of flexible non-elastic material such as polyvinyl chloride, polyvinylidene chloride, polyethylene or other suitable plastic sheet material. The two end connectors 24, 26 are secured to the opposite ends of tube 22, and the sheath 28 is secured to the end connectors 24, 26 over the elastic tube 22, by any suitable means, such as by clamps or ligatures 29 and 30, respectively. The two ends of the sheath 28 are substantially of the same diameter as the outer diameter of the inflatable tube 22 and its end connectors 24 and 26; but the internal diameter of the sheath increases towards its center so as to provide an internal volume substantially greater than the enclosed portion of the elastic tube 22 when the tube is non-inflated.

It will thus be seen that when elastic tube 22 is non-inflated, the sheath 28 thereover, being flexible but non-elastic, will tend to collapse around the outer face of the elastic tube 22, as shown in full lines in FIG. 1. The characteristics of the inflatable tube 22, particularly its wall thickness, are selected so that the tube does not begin to inflate until the prescribed pressure for infusion is reached. Thus, when the pumping bulb 10 is operated to inflate bladder 6 within the bag-presser 4, elastic tube 22 within the accumulator unit 20 will remain in its deflated state, as illustrated in full lines in FIG. 2; but as soon as the prescribed pressure within bladder 6 is reached, tube 22 will begin to inflate as shown in broken lines in FIG. 2. Since the increased quantity of air being pumped into the apparatus by operating the bulb 10 is now taken up by the inflation of the tube 22, the pressure within bladder 6 and tube 22 remains relatively constant until the inflation of tube 22 is limited by the substantially non-elastic sheath 28. Thus, sheath 28 not only limits the inflation of the elastic tube 22, but also provides a clear indication when the prescribed pressure is about to be exceeded, this indication being provided both by "feeling" the increase in the resistance to the operation of the pumping bulb at this point, and also by visually noting the inflation of the sheath to its full volume. Since this point, during the operation of the pumping bulb 10, is clearly indicated both to the operator and to other observers, the possibility that the infusion bag 2 may be over-pressurized, which could result in injury to the patient, is very substantially reduced. In fact, in many cases it may even be possible to dispense with the manometer 18 for indicating the infusion pressure.

It will be appreciated that once the bladder 6 of the bag-presser unit 4, and the inflatable tube 22 of the accumulator unit 20, have both been inflated by the use of the pumping bulb 10, the pressure of bladder 6 will be continuously applied to the infusion bag 2 by virtue of the flexible sleeve 8 maintaining the infusion bag tightly pressed against the bladder. As the volume of the infusion bag 2 decreases, pressurized gas within the inflatable tube 22 of the accumulator unit 20 will be transferred to the bladder 6 to make-up for the loss in volume of the infusion bag 2, thereby maintaining the pressure on the infusion bag relatively constant until the complete contents of the infusion bag have been administered to the patient.

Besides the above-described advantages provided by the accumulator unit 20, in maintaining the infusion bag 2 at substantially a constant pressure for the complete administration of the infusion liquid, and also in producing a clear indication of when the prescribed pressure is to be exceeded, thereby lessening the possibility of inadvertently over-pressurizing the infusion liquid, the accumulator unit 20 also permits improvements to be made in the construction of the bag-presser itself. One important advantage is that it permits the bag-presser to be constructed much more compactly, since a large volume is no longer necessary within the inflatable bladder 6, as part of the air volume is now taken up by the inflatable tube 22.

Figure 3:
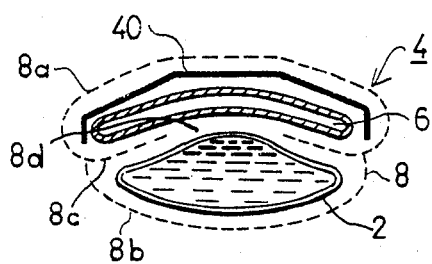
FIG. 3 is a transverse sectional view, along lines III—III of FIG. 1, illustrating the construction of the pressure-bag in the apparatus of FIG. 1.
Figure 4:
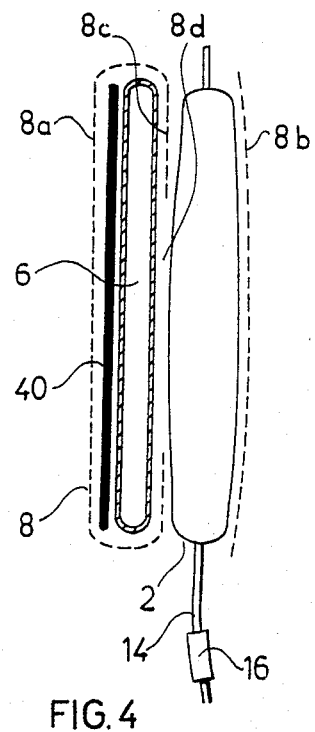
FIG. 4 is a longitudinal sectional view along lines IV—IV of FIG. 1.

FIGS. 3 and 4 illustrate the construction of the bag-presser 4 in the apparatus of FIG. 1 providing this advantage.

Thus, the bag-presser 4 illustrated in FIGS. 3 and 4 includes the above-mentioned inflatable bladder 6 and flexible sleeve 8 for maintaining the infusion bag 2 firmly pressed against the bladder. The bag-presser 4, however, further includes a rigid backing plate 40, which may be of metal (e.g., aluminum) or plastic. Rigid plate 40 is bent along its longitudinal axis to provide a generally concave face for receiving the inflatable bladder 6, as shown particularly in FIG. 3. The flexible sleeve 8, which retains the infusion bag 2 firmly pressed against the inflated bladder 6, is formed with three walls, namely an outer wall 8a enclosing the outer face of the rigid plate 40, a second outer wall 8b enclosing the infusion bag 2, and an intermediate wall 8c between the infusion bag 2 and the bladder 6. This intermediate wall 8c is preferably formed with an opening or window 8d so that the mid-portion of the infusion bag 2 is firmly pressed directly against the mid-portion of the bladder 6.

It has been found that such an arrangement not only permits the bag-presser 4 to be of a much more compact construction than the previously-known bag pressers, but also causes the pressure applied to the infusion bag 2 to more closely conform to the pressure within the bladder 6. Since the bladder 6 is in direct communication with the inflatable tube 22 of the accumulator unit 20, it will be appreciated that the pressure within the bladder 6, and thereby the pressure within the infusion bag 2, will be retained substantially constant even as the volume within the infusion bag 2 decreases during the course of the infusion.

Figure 5:
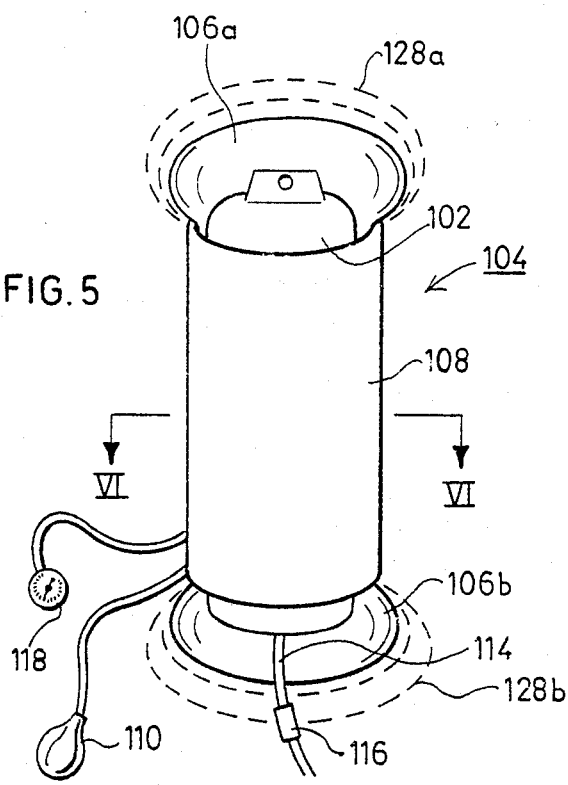
FIG. 5 illustrates a second embodiment of the invention wherein a single inflatable bladder serves both the functions of the bag-presser and of the accumulator in the apparatus of FIG. 1.
Figure 6:
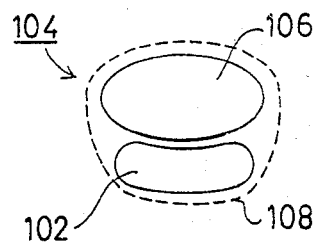
FIG. 6 is a transverse sectional view along lines VI—VI of FIG. 5.

Embodiment of FIGS. 5 and 6

FIGS. 5 and 6 illustrate another embodiment of the invention, wherein the function of the inflatable bladder 6 of the bag-presser 4, and the function of the inflatable tube 22 in the accumulator unit 20, are both performed by a single, elastic, inflatable bladder.

Thus, as shown in FIG. 5, the infusion bag, therein designated 102, is used with a bag-presser generally designated 104 and including an inflatable bladder 106 and a flexible sleeve 108. As in FIGS. 1-3, the bladder 106 is inflated by the use of a pumping bulb 110, and the infusion bag 102 is connected, via a tube 114 and drip chamber 116, to the patient receiving the infusion, the pressure applied to the infusion bag during the infusion being indicated by manometer 118.

As indicated earlier, the bag-presser 104 in FIGS. 5 and 6 also includes means for performing the function of the accumulator unit 20 of FIGS. 1-3. For this purpose, the inflatable bladder 106 is of subtantially longer dimension than the flexible sleeve 108, so that the bladder projects beyond the sleeve at both ends of the sleeve, as shown by projections 106a and 106b in FIG. 5. These projections define the accumulator portions of the elastic inflatable bladder 106 for accumulating the pressurized fluid pumped by the bulb 110. Each of these accumulator portions 106a, 106b is enclosed by a sheath 128a, 128b of flexible non-elastic material, corresponding to the material of sheath 28 in FIGS. 1-4. Each sheath has an internal volume larger than the non-inflated accumulator ends of the bladder 106, such that the sheaths are normally in a collapsed or deflated condition but assume an inflated state when the ends 106a, 106b are inflated to a predetermined volume. The sheaths thus limit the accumulation of the pressurized air in these ends, and also serve to indicate both visually and "by feel", when the pressure within the inflated accumulator ends of the bladder is about to exceed the prescribed pressure to be applied to the infusion bag 102.

In the apparatus illustrated in FIGS. 5 and 6, the sleeve 108 is a simple flexible sleeve which retains the infusion bag 102 firmly pressed against only the mid-portion of bladder 106 with the accumulator end portions 106a, 106b of the bladder projecting beyond, and therefore not engaged with, the ends of the infusion bag. Accordingly, when bulb 110 is operated to pump air into the bladder 106, the bladder is inflated until the pressure of the air within reaches the prescribed pressure to be applied to the infusion bag 102. Further operation of the pumping bulb 110 causes the bladder ends 106a, 106b, being unrestrained by the flexible sleeve 108, to further inflate until these ends engage their overlying sheaths 128a, 128b of non-elastic flexible material, at which time the further inflation of the bladder ends 106a, 106b is limited. As in the case of the embodiment illustrated in FIGS. 1-4, this point in the inflation of the bladder 106 is clearly indicated by the full inflation of the sheaths 128a, 128b, and also by the increase in the resistance to the pumping action produced by the sheaths limiting further inflation of the bladder ends 106a, 106b. During the dispensing of the liquid from the infusion bag 102, the decrease in the volume of the infusion bag will be taken-up by the pressurized air in the accumulator ends 106a, 106b of the bladder, thereby assuring that the liquid will be dispensed from the infusion bag at a substantially uniform pressure until the bag has been substantially emptied, as also described with respect to the FIGS. 1-4 embodiment.

Figure 7:
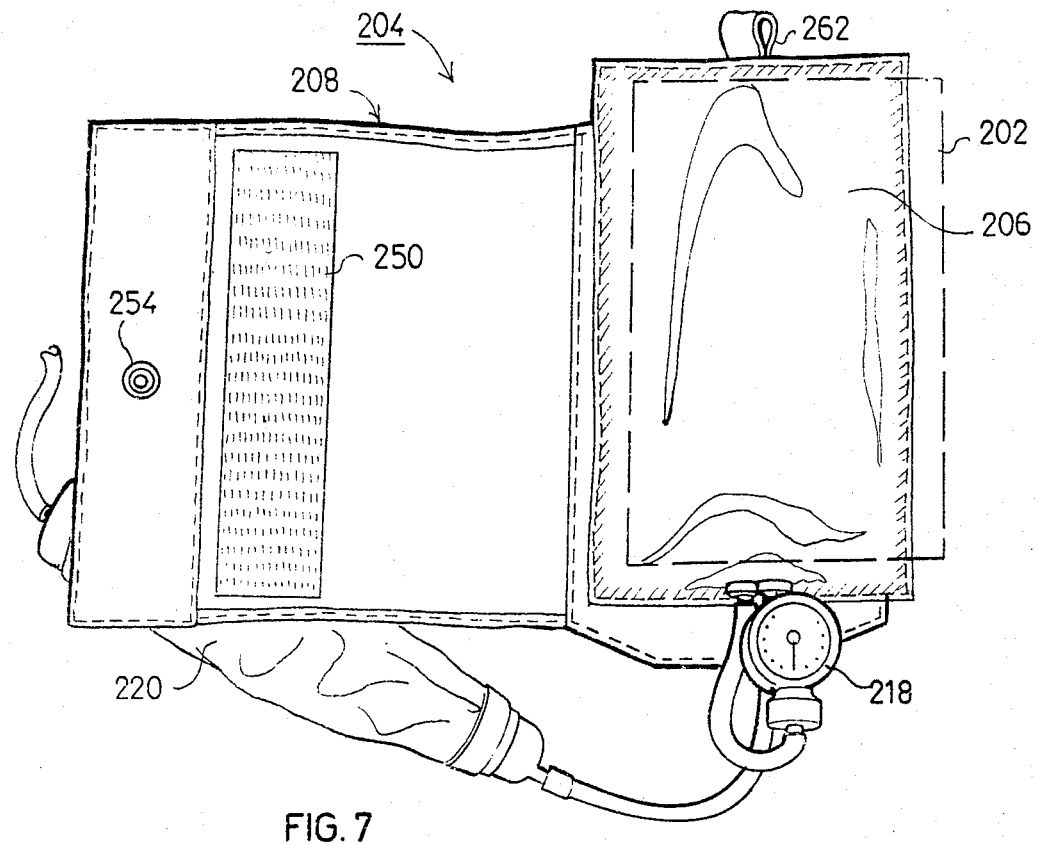
FIG. 7 illustrates another form of inflatable bag-presser unit constructed in accordance with the invention.
Figure 8:
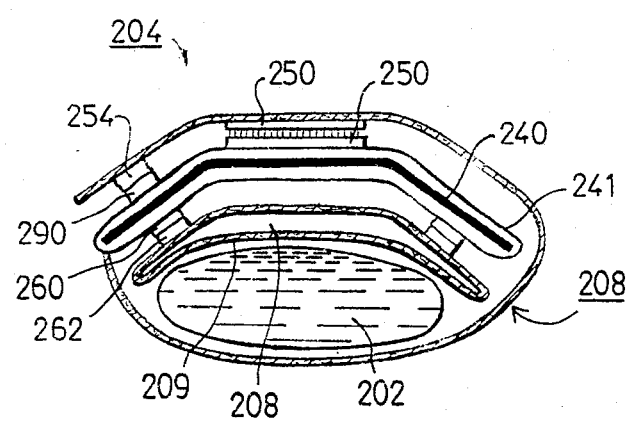
FIG. 8 is a transverse sectional view of the unit of FIG. 7 during its use for inducing flow from an infusion bag.

Embodiment of FIGS. 7 and 8

The bag-presser unit illustrated in FIGS. 7 and 8 is generally designated 204 and includes an inflatable bladder 206, a rigid backing plate 240 on one side of the bladder, and a flexible sleeve, generally designated 208, adapted to enclose the infusion bag 202 and to retain it pressed against the opposite side of the inflatable 206. The complete apparatus further includes a manometer 218 to indicate the pressure of the inflated bladder 206, and an accumulator unit 220 which provides the important advantages described above.

In the novel bag-presser unit 204 illustrated in FIGS. 7-8, the inflatable bladder 206 is enclosed within a flexible fabric sleeve 207; and similarly, the rigid backing plate 240 is also enclosed within a flexible fabric sleeve 241. Further, the overall sleeve 108 which encloses all the foregoing elements, including the infusion bag 202, is in the form of a flexible fabric strip secured at one end 209 to one end of the flexible sleeve 241 of the backing plate 240. Flexible strip 208 is then wrapped around the opposite end of the rigid backing plate 240 and is releasably attached by releasable fastening means to the upper face of the rigid backing plate sleeve 241.

As shown particularly in FIG. 8, the releasable fastening means comprises a plastic strip 250 of interlocking hooks and projections secured to the inner face of the flexible strip 208, and a mating plastic strip 252 secured to the outer face of the rigid backing plate sleeve 241. These interlocking plastic strips may be "Velcro" (Reg.T.M.) strips.

The releasable fastening means further includes snap fasteners 254 and 256 applied to the outer extremity of the outer strip 208 and the outer face of the rigid backing plate sleeve 241. In addition, sleeve 207 for the inflatable bladder 206 is also provided with releasable snap-fasteners 258 cooperable with fasteners 260 on the inner face of the rigid backing plate sleeve 241, to permit attachment and detachment of the inflatable bladder to the rigid backing plate. Further, the flexible sleeve 207 for the bladder 206 includes a loop 262 (FIG. 7) for suspending the inflatable bag-presser unit during use.

In order to use the illustrated device, inflatable bladder 206 is first attached to the rigid backing plate 240 by fasteners 258 and 260; the infusion bag 202 is placed against the inflatable bladder 206; and the flexible strip 208 is then wrapped around the infusion bag 202 and is secured to the unit in the form of a sleeve by the plastic strip fasteners 250, 252 and by the snap-fasteners 254, 256.

While the invention has been described with respect to three preferred embodiments, it will be appreciated that many other variations, modifications and applications of the invention may be made. For example, in the FIGS. 1-4 embodiment, the window 8d may be closed by an elastic strip to prevent the accidental removal of bladder 6 from its compartment while still permitting the bladder to conform to the shape of the bag. Further, the arrangement illustrated in FIGS. 5 and 6 could be similar to that of FIGS. 1-4 in the above respects.

Many other variations, modifications and applications of the invention will be apparent.

What is claimed is:

1. Apparatus for the induced infusion of a liquid from a flexible liquid bag, comprising:
   a hand-operable pumping bulb;
   elastic inflatable means coupled to said bulb for inflation by a fluid pumped therein by operating said bulb;
   and a sleeve for retaining the bag firmly pressed against a first portion of said elastic inflatable means for applying the pressure thereof to said bag in order to induce infusion of the liquid therefrom;
   characterized in that a second portion of said inflatable means serves as an accumulator for accumulating pressurized fluid pumped by said bulb, and comprises an outer non-elastic sheath enclosing said latter portion of the elastic inflatable means for limiting the accumulation of the pressurized fluid therein.

2. The apparatus according to claim 1, wherein said non-elastic sheath is of flexible material having a substantially larger internal volume than the enclosed portion of the elastic inflatable means, such that the sheath is normally deflated but also assumes an inflated condition when the enclosed portion of the elastic inflatable means has been inflated to a predetermined volume and pressure, thereby indicating when a predetermined pressure, applied to the elastic inflatable means and to said liquid bag, is about to be exceeded.

3. The apparatus according to claim 1 wherein said first and second portions of the elastic inflatable means are separate inflatable units, said first portion being an inflatable bag-presser unit against which the liquid bag is pressed by said flexible sleeve, and said second portion being a separate inflatable accumulator unit enclosed by said outer sheath.

4. The apparatus according to claim 3, wherein said inflatable accumulator unit includes an inflatable tube enclosed by said outer sheath.

5. The apparatus according to claim 4, wherein said outer sheath is of flexible material of substantially larger volume than that of said inflatable tube, such that the sheath is normally deflated but also assumes an inflated condition when the enclosed tube has been inflated to a predetermined volume and pressure.

6. The apparatus according to claim 3, wherein said inflatable bag-presser unit includes an inflatable bladder and a rigid backing plate on one side of said bladder, said sleeve being flexible and adapted to receive said liquid bag and to retain same pressed against the opposite side of said inflatable bladder.

7. The apparatus according to claim 6, wherein said rigid backing plate is bent so as to form a generally concave face for receiving the inflatable bladder and the liquid bag.

8. The apparatus according to claim 6, wherein said flexible sleeve includes a first portion enclosing both said rigid backing plate and said inflatable bladder, and a second portion enclosing only said liquid bag but including an opening such as to bring a portion of the surface of the bag into direct contact with the bladder.

9. The apparatus according to claim 1, wherein both said first and second portions of the elastic inflatable means are constituted of a single unit including an elastic bladder enclosed at its mid-portion by said sleeve such as to retain the liquid bag pressed against said mid-portion of the bladder, at least one end of said bladder projecting outwardly of said sleeve and serving as said accumulator for accumulating the pressurized fluid, said projecting end of the bladder being enclosed by said non-elastic sheath.

10. Apparatus according to claim 9, wherein both ends of said bladder project outwardly of said sleeve and serve as accumulators for accumulating the pressurized fluid, both of said projecting ends of the bladder being enclosed by a non-elastic sheath.

11. An inflatable bag-presser unit for use with with an infusion bag, comprising: an inflatable bladder, a rigid backing plate on one side of said bladder, and a flexible sleeve adapted to receive said infusion bag and to retain same pressed against the opposite side of said inflatable bladder, said rigid backing plate being bent so as to form a generally concave face for receiving the inflatable bladder and the infusion bag, said sleeve being in the form of a flexible strip wrappable about said rigid backing plate to enclose the inflatable bladder and infusion bag within said generally concave face of the rigid backing plate, said rigid backing plate being enclosed within a backing plate sleeve, said flexible strip being secured at one end to said backing plate sleeve, and at the opposite end being releasably attached to the backing plate sleeve by releasable fastening means.

12. The bag-presser unit according to claim 11, wherein said releasable fastening means comprises snap-fasteners between the inner face of the flexible strip and the outer face of the rigid backing plate sleeve.

13. The bag-presser unit according to claim 11, wherein said releasable fastening means comprises strips of interlocking plastic hooks and projections on the inner face of said flexible strip and on the outer face of said backing plate sleeve.

14. The bag-presser unit according to claim 11, wherein said releasable fastening means comprises both snap-fasteners and plastic strips of interlocking hooks and projections on the inner face of said flexible strip and on the outer face of said rigid backing plate sleeve.

15. The bag-presser unit according to claim 11, wherein said inflatable bladder is also enclosed within a flexible sleeve and includes releasable fasteners for releasably attaching same to the rigid backing plate sleeve.

16. The bag-presser unit according to claim 15, wherein said bladder flexible sleeve includes a loop for suspending the inflatable bag-pressure unit and the infusion bag during use.

* * * * *

UNITED STATES PATENT AND TRADEMARK OFFICE
CERTIFICATE OF CORRECTION

PATENT NO. : 4,507,116

DATED : March 26, 1985

INVENTOR(S) : Saul Leibinsohn

It is certified that error appears in the above-identified patent and that said Letters Patent is hereby corrected as shown below:

Cover Page, Column 1, in (30) FOREIGN APPLICATION PRIORITY DATA, add -- August 27, 1982 (IL) Israel........66665 --.

Column 7, line 30, "108" should read -- 208 --.

Column 10, line 7, in last line of Claim 12, delete "rigid".

Signed and Sealed this

Sixth Day of January, 1987

Attest:

DONALD J. QUIGG

*Attesting Officer*  *Commissioner of Patents and Trademarks*